(12) United States Patent
Porche et al.

(10) Patent No.: US 6,371,464 B1
(45) Date of Patent: Apr. 16, 2002

(54) VALVE SPRING

(75) Inventors: Leonard Porche, Simi Valley; William Jeff Bertrand, Ventura; Mitchell Solis, Camarillo, all of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/579,298

(22) Filed: May 25, 2000

Related U.S. Application Data

(60) Provisional application No. 60/179,626, filed on Feb. 2, 2000.

(51) Int. Cl.⁷ .............................. A61M 5/00; F16F 1/08

(52) U.S. Cl. ................. 267/166.1; 267/156; 267/166; 29/896.9; 148/908; 604/9

(58) Field of Search .............................. 267/166.1, 167, 267/168, 166, 158, 161, 156, 155, 180, 204; 72/135, 136, 371; 148/580, 645, 908; 29/896.9; 600/585; 604/8, 9, 264, 523, 95.04, 528, 247

(56) References Cited

U.S. PATENT DOCUMENTS

| | | | | |
|---|---|---|---|---|
| 2,390,937 A | * | 12/1945 | Holland | 29/896.9 |
| 3,300,042 A | * | 1/1967 | Gordon | 267/166.1 |
| 3,819,169 A | * | 6/1974 | Imme et al. | 267/156 |

* cited by examiner

*Primary Examiner*—Douglas C. Butler
(74) *Attorney, Agent, or Firm*—Curtis D. Kinghorn; Harold R. Patton

(57) ABSTRACT

A method of making a spring are described. The spring is made by etching or cutting at least one spiral arm in a flat substrate leaving residual material around the arm. The intermediate residual material is either pushed or lifted to form a conical spring.

50 Claims, 6 Drawing Sheets

VALVE SPRING

This application claims the benefit of U.S. provisional application Ser. No. 60/179,626 filed Feb. 2, 2000.

BACKGROUND OF THE INVENTION

1. Field of the Invention

This invention relates generally to surgically implanted physiological shunt systems and related flow control devices. More particularly, the present invention relates to a spring in a shunt system including a one-way flow control valve for controlling the flow of cerebrospinal fluid out of a brain ventricle and preventing backflow of fluid into the brain ventricle.

2. Description of Related Art

In the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children where fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube that conducts the fluid away from the brain to be reintroduced into the peritoneal cavity or into the vascular system, as by extending a distal catheter through the patient's jugular vein to the atrium portion of the heart.

To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of overdrainage of the cerebrospinal fluid from the brain ventricles sometimes exists. Overdrainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter.

This overdrainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such overdrainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

It is desirable in some instances to permit the physician to be able to alter the flow characteristics through the drainage system after it has been subcutaneously implanted. To this end, on-off devices have been provided for implantation as a portion of the fluid conduit as an additional element of the shunt. An exemplary on-off device is shown in U.S. Pat. No. 3,827,439. Moreover, flow control devices have been provided which utilize a plurality of flow control valves having different flow control characteristics, which provide, alternative fluid pathways therethrough such that selection of a desired fluid pathway can be made by the selective percutaneous manipulation of the device when subcutaneously implanted. Such flow control devices having selectable alternative fluid pathways are shown in U.S. Pat. Nos. 5,154,693 and 5,167,615, the contents of which are incorporated herein in their entireties by reference.

These prior fluid shunt devices have all shared one important limitation: they only permit fluid flow therethrough upon achieving at most two fluid pressure differentials at the inlet and outlet of the device. In treating hydrocephalus, however, it is often desirable to vary the device "opening" pressure differential in accordance with ventricle size and treatment objective. For example, initial treatment may require a lower than normal pressure differential to initiate shrinkage of the ventricles, but as the ventricles decrease in size, the pressure differential should be increased gradually so that when the ventricle is returned to normal size the intraventricular pressure is at its normal value and the intracranial force systems are in balance (i.e., the opening differential pressure is set at a level that will stabilize the ventricles at a desired size). Generally speaking, the opening differential pressure should be varied inversely with the ventricle size. It is desirable to leave a lower pressure valve in a patient after the ventricles are again normal size, because the ventricles can further collapse, leading to a condition known as "slit" ventricles.

A further reason for providing adjustability in the opening pressure differential is to correct for variations in nominal opening pressure differentials typical in manufactured valves. With an adjustable valve, the opening pressure differential can be more accurately set at the factory and can be checked and corrected if necessary in the operating room prior to implantation.

Accordingly, there was a need in the medical arts for convenient and effective physiological drainage systems for controlling the flow of fluid from one part of the body to another, which are relatively inexpensive to manufacture, permit fluid flow therethrough only when upstream fluid pressure exceeds downstream fluid pressure by a selected pressure differential, and also provide means for altering the selected pressure differential by percutaneous manipulation of the device when it is subcutaneously implanted. Moreover, such a flow control device was needed that incorporates an integral siphon control device that opens only in response to positive upstream fluid pressure, and re-closes or remains closed in the absence of such positive upstream fluid pressure or in response to negative downstream hydrostatic pressure on the device.

These objectives were met in the invention described in U.S. Pat. No. 5,637,083, issued Jun. 10, 1997 to William J. Bertrand and David A. Watson entitled "IMPLANTABLE ADJUSTABLE FLUID FLOW CONTROL VALVE", assigned to the assignee of the present invention, the contents of which are incorporated herein in its entirety. The invention described in the '083 patent resides in an improved subcutaneously implantable and percutaneously adjustable fluid flow control device useful in a physiological shunt system for controlling the flow of fluid from one part of the body to another. The fluid flow control device includes components responsive to an external or percutaneously-applied magnetic field, to provide the device a variety of pressure/flow characteristics.

In accordance with the invention described in the '083 patent, the fluid flow control device comprises an inlet, an outlet and valve means for controlling the fluid flow from the inlet to the outlet. The valve means comprises a valve housing including a fluid passageway therethrough that has a peripheral surface that forms a valve seat, and a valve element having a diameter larger than the valve seat. Means are provided for biasing the valve element against the valve seat so as to keep the fluid passageway closed until a fluid pressure differential between the inlet and the outlet exceeds a selected valve opening pressure. Further, a pump is situated between the inlet and the valve means. The pump provides means for flushing fluid through the device by the application of percutaneous pressure to the pump.

In one preferred form of the invention of the '083 patent, the valve housing includes a threaded aperture and a flow regulator insert which is threaded into the aperture to define the fluid passageway. Means are provided for adjusting the amount of bias applied to the valve element by the biasing means. In particular, the adjusting means includes a fixed dual concentric stair-step array and an overlying rotor assembly having a first surface which supports an end of a valve element-biasing spring, and a second surface which is supported by the stair-step array. The rotor assembly is adapted to rotate in response to an external or percutaneously-applied magnetic field and such rotation of the rotor assembly permits selected seating of the second surface on the stair-step array to raise or lower the rotor assembly with respect to the stair-step array.

The dual concentric stair-step array includes a central rotor pivot, a plurality of inner steps surrounding the rotor pivot, and a plurality of outer steps extending peripherally about the inner steps. The rotor assembly includes a magnet embedded within a base having an inner leg adapted to bear against a selected one of the plurality of inner steps, and outer leg disposed diametrically opposite the inner leg and adapted to bear against a selected one of the plurality of outer steps, a central aperture through which the rotor pivot extends, and a rotor cap fixed to the base on a side thereof opposite the inner and outer legs. The rotor cap provides the first surface of the rotor assembly and includes a central aperture aligned with the central aperture of the base, through which the rotor pivot extends.

A compression spring is provided between a portion of the valve housing surrounding the fluid passageway and the first surface of the rotor assembly. The compression spring biases the rotor assembly into contract with the dual concentric stair-step array.

Means are also provided for occluding a portion of the fluid flow control device adjacent to the inlet by application of manual percutaneous pressure to the device. Similarly, means are provided for occluding a portion of the fluid flow control device adjacent to the outlet also by application of manual percutaneous pressure to the device.

Moreover, a siphon control device is situated between the valve and the outlet.

In another preferred form of the invention of the '083 patent, means are provided for locking the rotor assembly into one of several possible rotational positions relative to the stair-step array to prevent rotation thereof Further, means are provided for disengaging the locking means to permit rotation of the rotor assembly in response to the external magnetic field. More particularly, the locking means comprises a pin having a first end that engages one of a plurality of detents in an outer peripheral surface of the rotor assembly to prevent rotation thereof.

The disengaging means comprises pin-actuating means for moving the pin between a first extended position, wherein the end of the pin engages one of the plurality of detents, and a second retracted position. The pin actuating means comprises a pivotable lever including a pin-engaging shaft that engages a second end of the pin, and a manually actuated lever disposed within the pump and biased so as to urge the pin into its first position.

SUMMARY OF THE INVENTION

A spring and a method of making a spring are described. The spring is made by etching or cutting at least one, but preferably two or more interleaved arms in a flat substrate leaving intermediate residual material between the arms or around the arm where there is only a single arm. The intermediate residual material is either pushed or lifted to form a conical spring.

It is an object of the present invention in one embodiment to provide a spring that has a linear compression versus spring constant range.

It is an object of the present invention in one embodiment to provide a spring that is substantially flat when fully compressed.

It is an object of the present invention in one embodiment to provide a method of making springs that allows several springs to be made concurrently.

It is an object of the present invention in one embodiment to provide a method of making springs that allows several springs to be made precisely.

It is an object of the present invention in one embodiment to provide a method of making springs that allows several springs to be made economically.

It is an object of the present invention in one embodiment to provide a method of making springs that allows several springs to be made reproducibility.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

Figure 5:
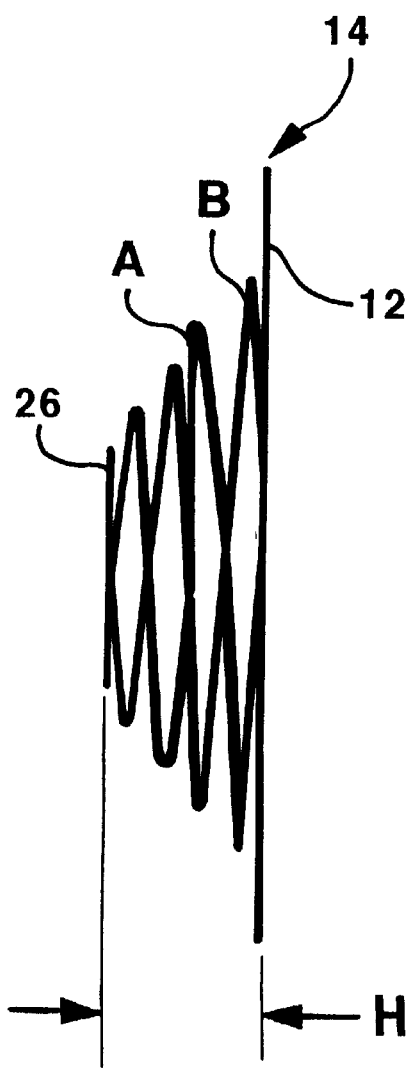
FIG. 5 is a side view of the spring of FIG. 1 is its extended configuration.

The spring of the present invention is shown in the Figures generally labeled 10. Spring 10 is preferably made from a pattern cut, punched or formed in a flat substrate 12 that is subsequently stretched to the desired final height as shown in FIG. 5. Substrate 12 is preferably a metal substrate. Examples of such metal substrates 12 include but are not limited to nickel chrome alloys such as Elgiloy® or Phynox®, stainless steel like 316 stainless steel, MP35N alloy, nickel-titanium alloys like Nitinol and titanium Elgiloy® alloy is available from Carpenter Technology Corporation of Reading Pa. Phynox® alloy is available from Metal Imphy of Imphy, France. Both Elgiloy® and Phynox® are cobalt-based alloys which also include chromium, iron, nickel and molybdenum. 316 stainless steel and MP35N alloy are available from Carpenter Technology Corporation and Latrobe Steel Company of Latrobe, Pa. Nitinol alloy is available from Shape Memory Applications of Santa Clara, Calif.

Preferably, metal substrate 12 has a thickness "T" of between about 0.0005" and 0.005" and more preferably has a thickness of about 0.001". Although substrate 12 is preferably a metal substrate, other materials may be used including but not limited to plastics, ceramics and composite materials. Whatever material substrate 12 is made of, substrate 12 should have the properties of a high modulus of deformation. That is, the material of substrate 12 should be able to be deformed and recover to its original shape for many cycles. Substrate 12 may be of any shape. But, spring 10 is preferably circular and has an outer peripheral edge 14.

A pattern is cut, punched or formed in substrate 12 entirely through substrate 12. This pattern is preferably an interleaved spiral having a first leg 16 and a second leg 18. First and second legs 16, 18 are preferably evenly spaced from one another and each has a proximal end 20 and a distal end 22. First and second legs 16, 18 preferably begin and end on opposite sides of a central point 24 at proximal and distal ends 20, 22 respectively, but do not touch. Although first and second legs 16, 18 preferably begin and end on opposite sides of central point 24 they are not required to do so.

When first and second legs 16, 18 are formed, a central area 26 around central point 24 between first and second legs 16, 18 is formed of the material of substrate 12. The size of central area 26 depends on how close the distal ends 22 of first and second legs 16, 18 come to central point 24. In addition, a residual area 28 is formed between the first and second legs 16, 18 at the proximal ends 20 of first and second legs 16, 18 and the peripheral edge 14.

First and second legs 16, 18 are preferably formed in substrate 12 by photo-etching first and second legs 16, 18 in the material of substrate 12. The preferred method to manufacture the spring 10 of the present invention is to use photo resist etching process sometimes called photo chemical etching as is well understood in the art. Though the manufacturing technology is well established for making printed circuit boards, it is believed to be unique for making springs. More particularly, it is believed that using the photo-etching method described herein is unique for making flat coil springs including such springs with multiple legs.

First and second legs 16, 18 may also be formed by cutting legs 16, 18 in substrate 12. This may be done by punching first and second legs 16, 18 in substrate 12 or by cutting first and second legs 16, 18 in substrate 12 by EDM, laser cutting and water jet cutting. Other methods of cutting first and second legs 16, 18 in substrate 12 will occur to those skilled in the art. As first and second legs 16, 18 are formed, intermediate residual material 30 from substrate 12 remains between respective portions of first and second legs 16, 18.

Once first and second legs 16, 18 are formed in substrate 12, spring 10 is formed by lifting or pushing central area 26 away from the residual area 28 until a desired free height "H" is reached for the spring 10. This lifting or pushing is preferably done by moving a plunger against the central area 26 while capturing or restraining the residual area 28 at or near peripheral edge 14. Spring 10 is then formed as the intermediate residual material 30 is stretched between central area 26 and residual area 28.

Alternately, the central area 26 and the residual area 28 may each be "captured" and then moved apart from each other so that the spring 10 is formed as the intermediate residual material 30 is stretched. Central area 26 and residual area 28 may be "captured" by mechanically grasping or clamping central area 26 and residual area 28.

Although using a plunger as described above is the preferred method of forming spring 10 and "capturing" and separating central area 26 from residual area 28 has been described, other methods may be used as will occur to those skilled in the art. As central area 26 is lifted or pushed above residual area 28, intermediate residual material 30 between first and second legs 16, 18 will also be pushed or lifted away from its flat configuration to form a cone-shaped spring 10 (FIG. 5). When spring 10 is in its extended configuration as shown in FIG. 5, intermediate residual material 30 forms the "coils" of the spring 10.

Figure 1:
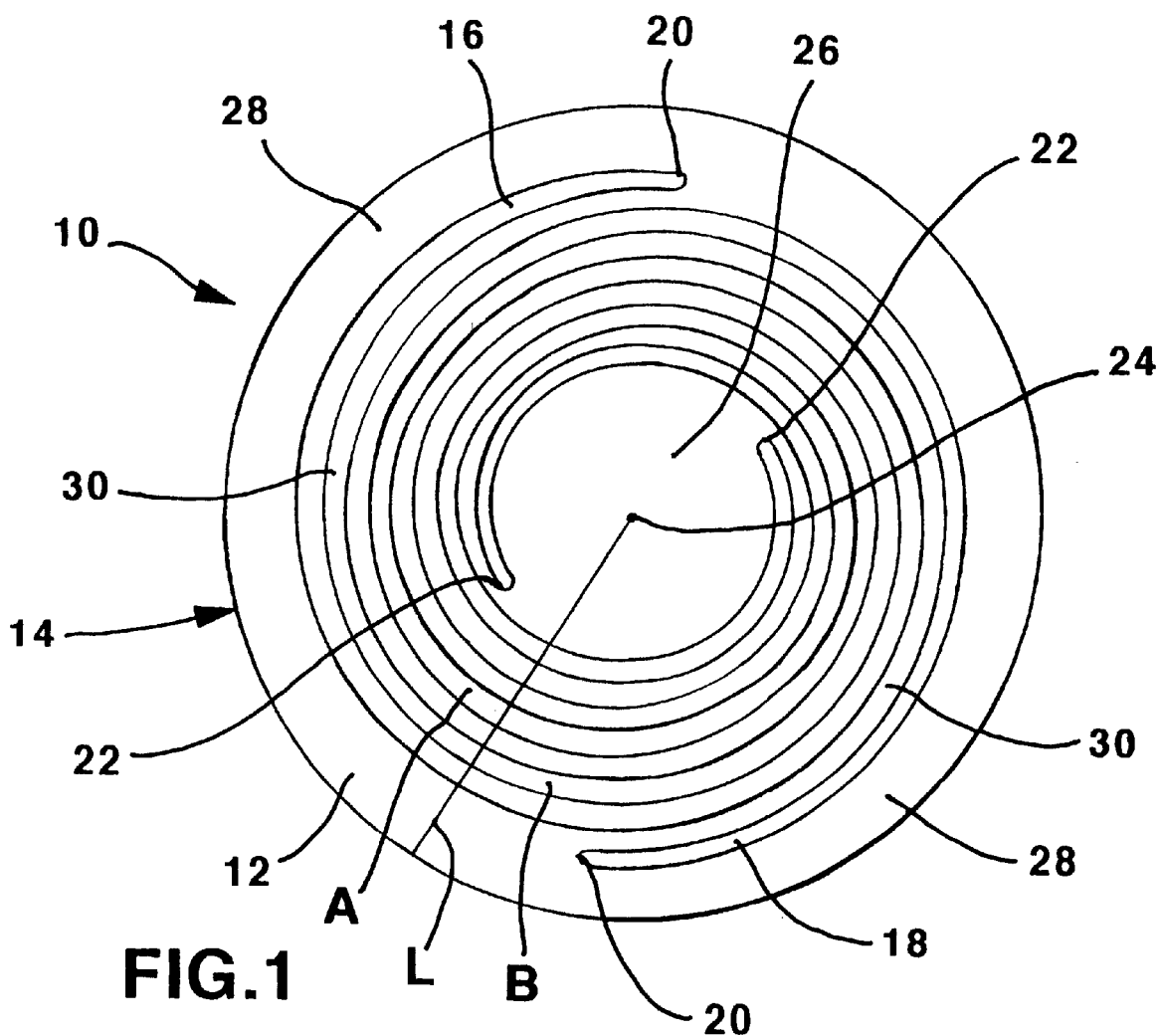
FIG. 1 is a top view of the spring of the present invention in its flat configuration.
Figure 2:
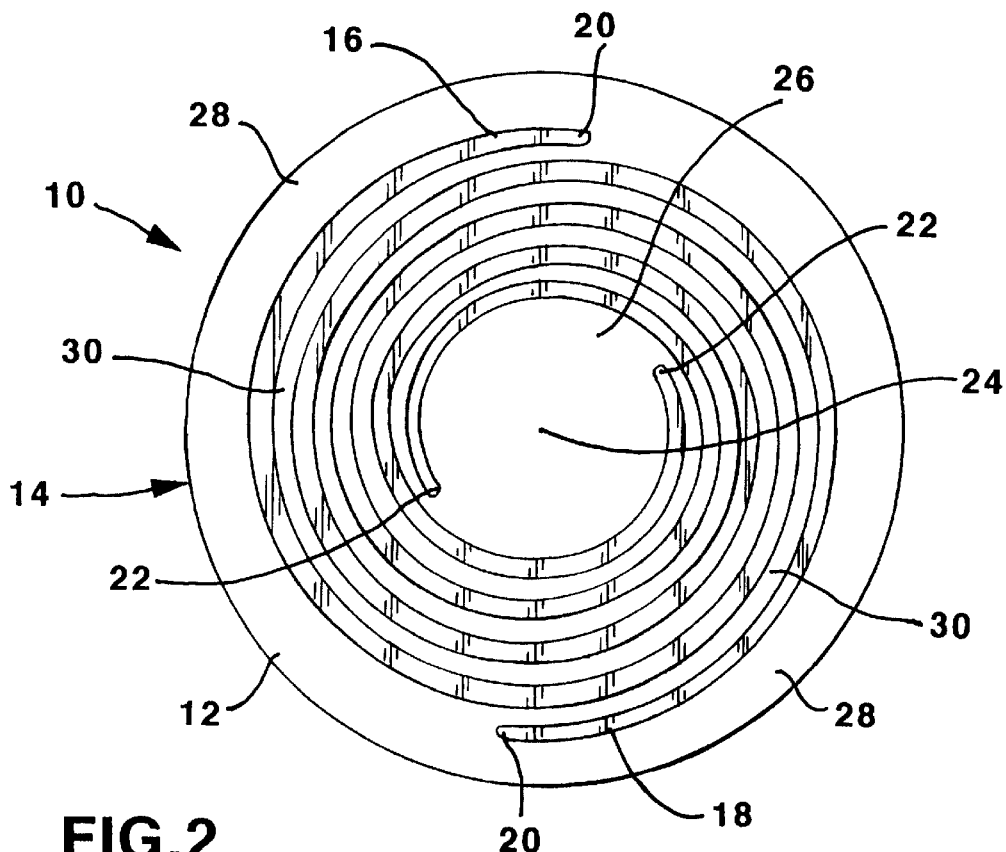
FIG. 2 is a top view of the spring of FIG. 1 with the first and second legs highlighted.
Figure 3:
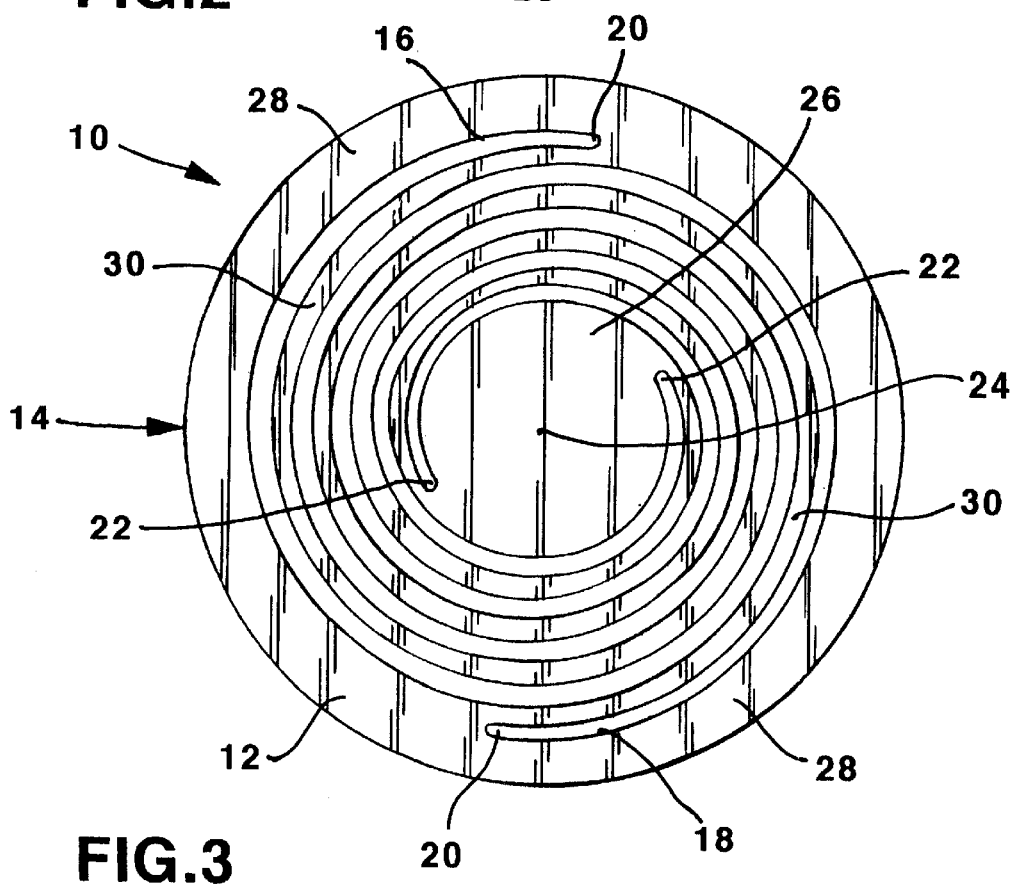
FIG. 3 is a top view of the spring of FIG. 1 with the intermediate residual material highlighted.
Figure 4:
FIG. 4 is a side view of the spring of FIG. 1 in its flat configuration.

Referring to FIGS. 1 and 2, the spring 10 in whatever embodiment shown provides several unique advantages. Because of the tapered or cone shape of spring 10, springs 10 are very space efficient. Proceeding on a line "L" extending from central point 24 to the peripheral edge 14, each "coil" formed by the intermediate residual material 30 ("A") can nest within the next larger one ("B"). This means that the compressed height is essentially the thickness of the substrate 12 itself. By contrast, a conventional coil spring made from wire would become coil bound as the coils nest on top of one another at full compression and have a solid, non-compressible height equal to the thickness of the wire times the number of coils.

A conically wound wire spring would be a partial solution to the nesting problem but has additional disadvantages. When an unloaded wire coil spring is compressed, there is a non-linear initial spring constant rate due to settling and closing of the open coils at the ends. With all wire springs, in order to get into the linear range of the compression distance vs. spring constant, extra space must be allowed in the assembly so that the spring 10 can be pre-loaded. It is necessary to "pre-load" traditional springs because the physical shape of the ends of the springs and the spacing of the ends of the springs from the load affect the spring constant of the spring in a non-linear way. As a result, when a traditional spring is first compressed, the ends of the coil of the spring must settle into contact with the load and the next spiral portion of the coil so that the spring operates in a linear fashion. This need to allow for a partial compression is not satisfactory for a device like the valve of the '083 patent described above which must have a linear spring rate and which has no extra space to accommodate pre-compression.

Figure 6:
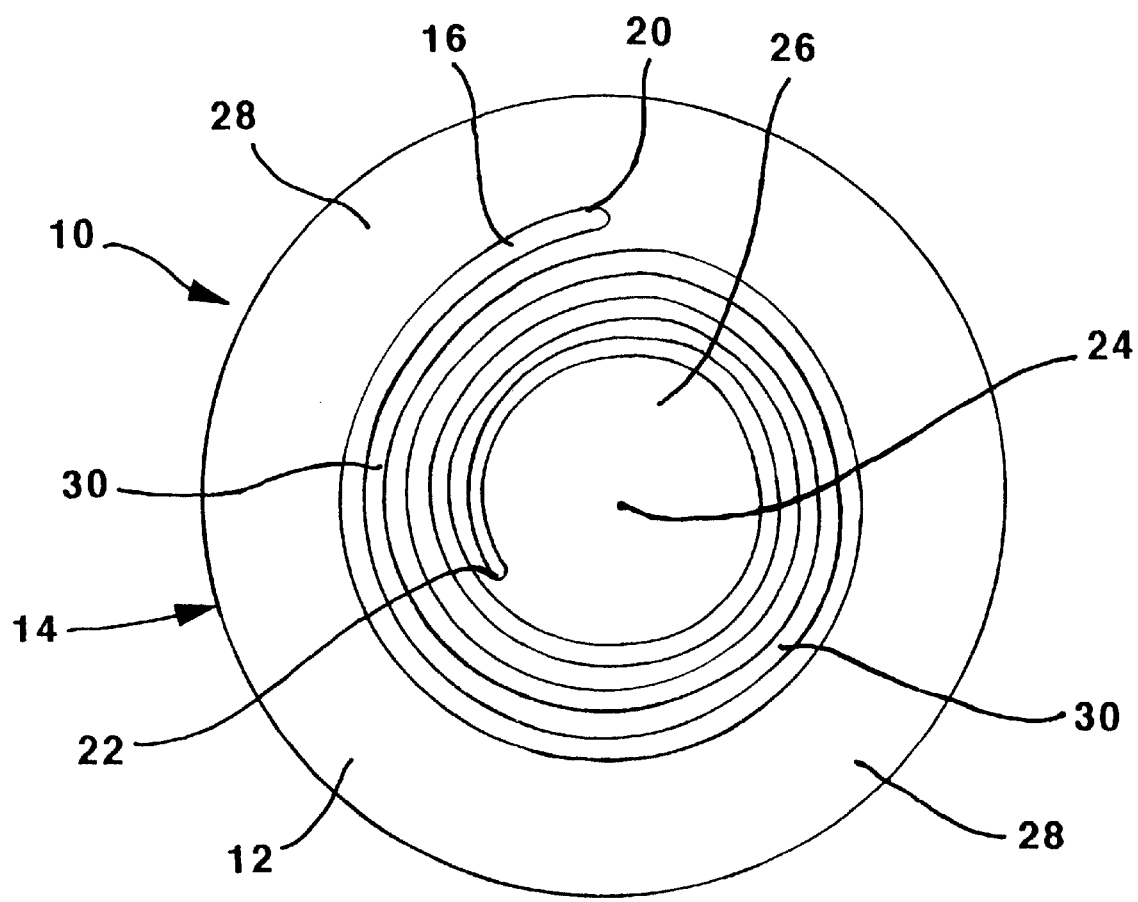
FIG. 6 is a top view of an alternate embodiment of the invention of FIGS. 1–5 showing one leg.

The flat spring design of the present invention includes central area 26 and distal ends 22 that do not require "settling" to achieve a linear compression distance vs. spring constant ratio. This means that the spring design of the spring 10 of the present invention performs in a completely linear fashion all the way from zero preload to full compression over it's entire free height "H". In fact, in the embodiment described above and shown in FIG. 6 where spring 10 has a relief cut in the central area 26, the spring 10 performs linearly under compression in a range greater than it's total free height "H". This allows the valve of the '083 patent to be built to the lowest possible profile. These advantages are not found in the prior art designs.

Use of the nesting design for spring 10 allows a valve formed using spring 10 to have a lower profile than if a conventional coil spring were employed. Where the valve is a shunt valve such as that used to control the flow of excess hydrocephalus fluid from a brain as described in the '083 patent above, having a low profile is very important to minimize the incidence of dermal abrasion and irritation when the valve is implanted in a patient.

An additional advantage of the present invention in one embodiment is that one or more than two legs may be incorporated into the spring 10. In the embodiment shown in FIG. 6, only a single leg 16 is formed in a spiral configuration. Leg 16 has a proximal and a distal end 20, 22 respectively. In this embodiment, the proximal and distal ends 20, 22 of legs 16 may begin and end anywhere along the periphery 14 or central area 26, respectively. As a result, there are an infinite number of angular relationships between proximal and distal ends 20, 22. In all other ways, the teachings above apply to this embodiment as well.

Figure 7:
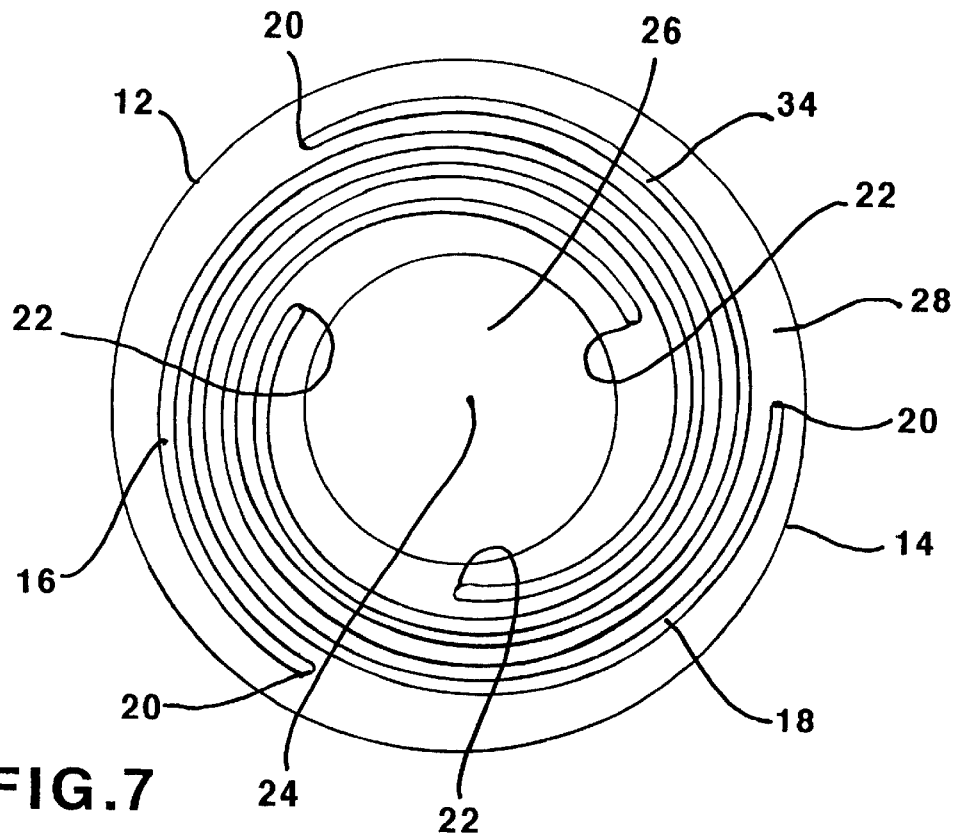
FIG. 7 is a top view of an alternate embodiment of the invention of FIGS. 1–5 showing three legs.

In the embodiment shown in FIG. 7, an additional leg 34 is formed also having a proximal and a distal end 20, 22 respectively. In this embodiment, the proximal and distal ends 20, 22 of legs 16, 18 and 34 are preferably spaced at 120° relative to each other but are not required to be. In all other ways, the teachings above apply to this embodiment. The advantage of this design is that the spring 10 will have a more stable base, that is, the spring 10 will sit more straight and stable on a flat surface than would a coil spring made according to known techniques.

Figure 8:
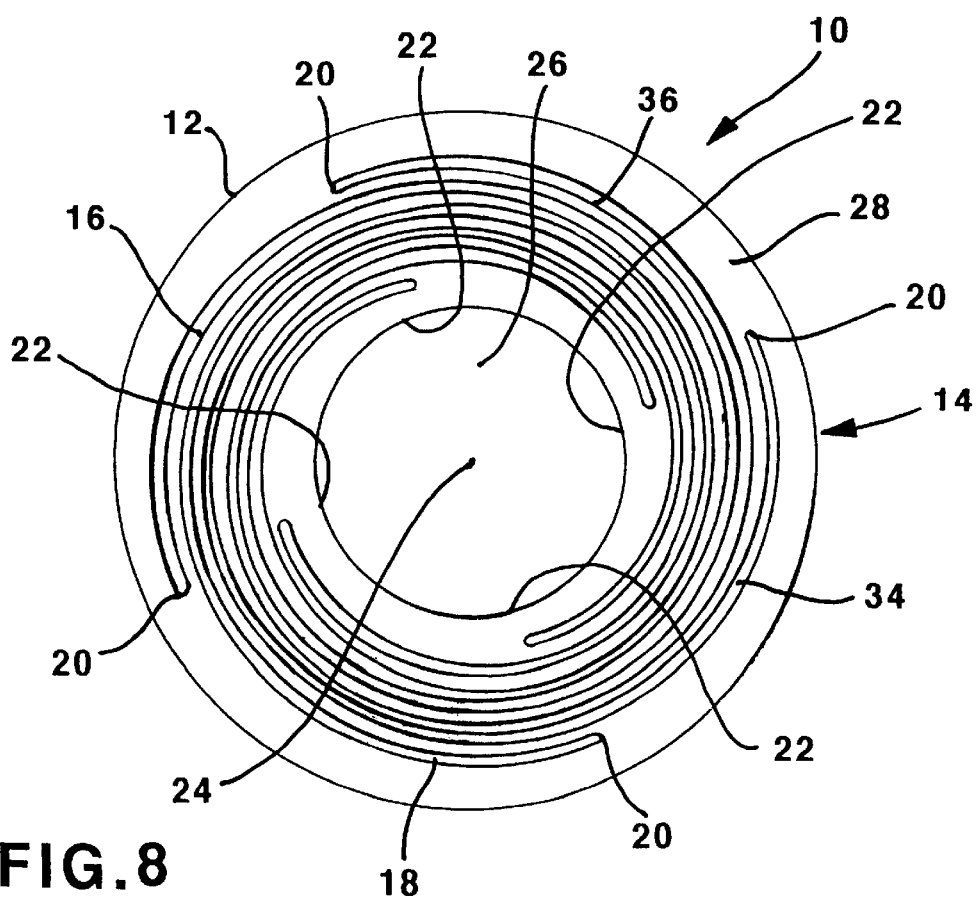
FIG. 8 is a top view of an alternate embodiment of the invention of FIGS. 1–5 showing four legs.

Although the embodiment of FIG. 7 shows three legs 16, 18 and 34, four of more legs may be used as desired. FIG. 8 shows an embodiment having four legs. Here, an additional leg 36 is added to the legs, 16, 18 and 34 of FIG. 7. Again, each leg 16, 18, 34 and 36 has a proximal and a distal end, 20, 22, respectively. In this embodiment, the proximal and distal ends 20, 22 are preferably spaced at 90° relative to each other but are not required to be. In all other ways, the teachings above apply as well to this embodiment. An advantage of this design is again that the spring 10 will also have a stable base.

Figure 9:
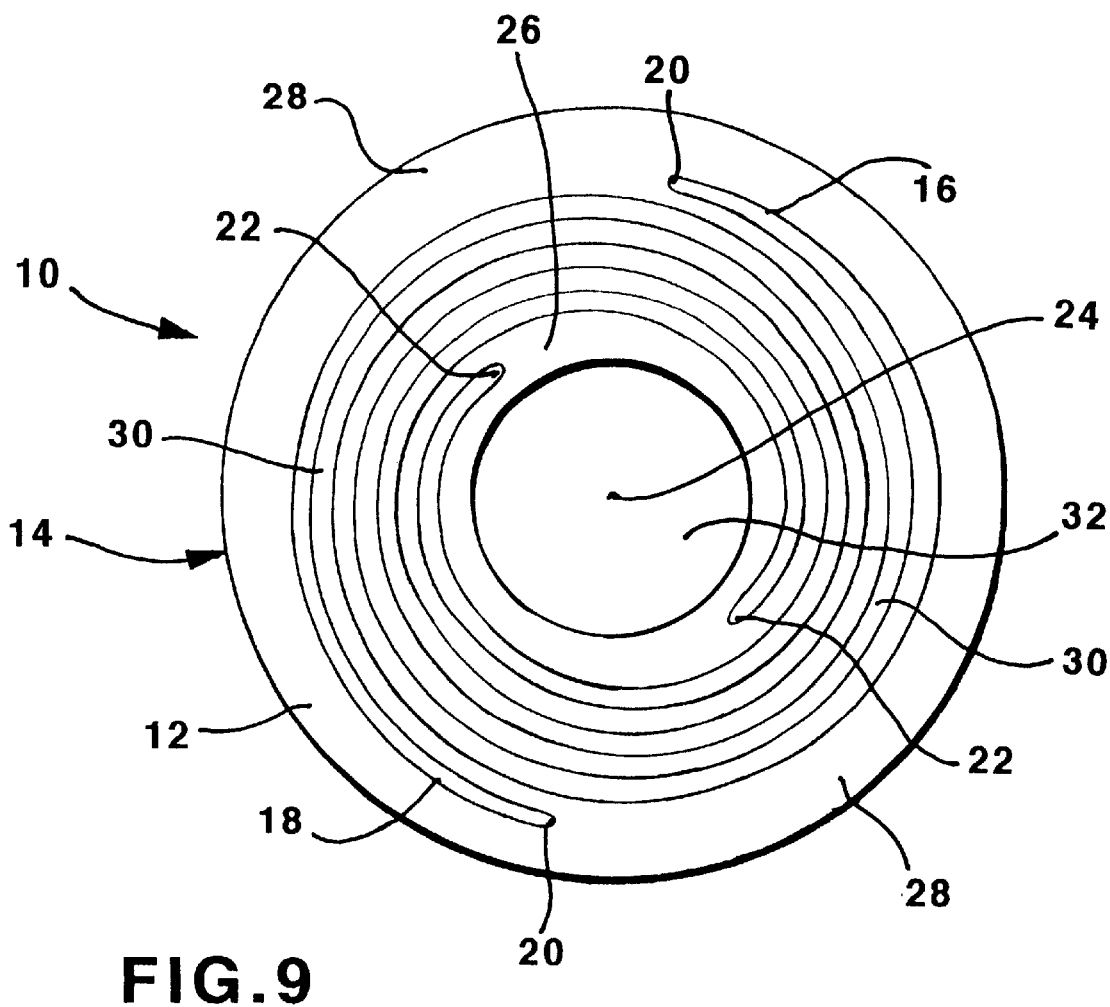
FIG. 9 is a top view of an alternate embodiment of the invention of FIGS. 1–8 where a hole is formed in the central area around the central point.

FIG. 9 shows an alternate embodiment of the invention of FIGS. 1–8. In this embodiment, central area 26 has a hole 32 formed around central point 24. Hole 32 is cut, punched or etched entirely through central area 26. Hole 32 allows the central area 26 to receive and position a ball or other object with respect to the central area 26. If desired, hole 32 may have any desired shape in addition to circular.

Figure 10:
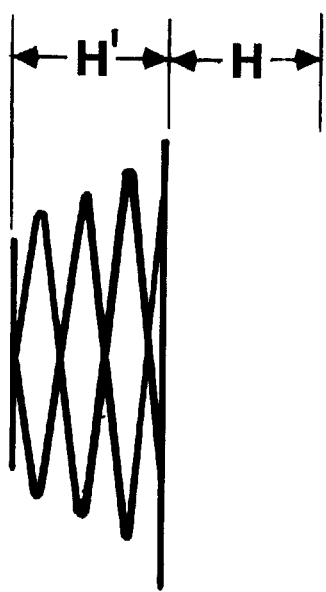
FIG. 10 is a side view of the spring of FIGS. 1–9 with the central area pushed below the peripheral edge 14.

FIG. 10 shows the spring 10 of FIGS. 1–9 with the central area 26 moved past and below the plane containing the peripheral edge 14 in a negative direction to a height "H". This allows spring 10 to have a travel greater than 100% of the height "H". As a result, the spring 10 is able to perform linearly under compression in a range greater than it's total free height "H". This feature may have particular utility where spring 10 is a pressure regulating spring.

Another advantage of the present method of making springs 10 is that many springs 10 can be made concurrently including over 100 at a time. Currently, coil wire springs are made by winding wire on special spring making machines one at a time. Though these machines can have very high throughput, each spring will be slightly different from the one before or after it. Therefore, there is a lot of "art" in the fabrication of conventional wire spring manufacturing.

The photo-etching method of the present invention allows all the springs 10 to be made from a single pattern. By replicating a large number of identical patterns onto a large piece of sheet stock of substrate 12 material, many, many springs 10 can be fabricated simultaneously. This reduces the number of variables from spring to spring while at the same time being extremely economical. All of these advantages are true for springs 10 in general but are more particularly true for springs 10 used in adjustable valves such as is described in the '083 patent where reproducibility in springs 10 used in such valves is critical to accurate valve operation. Thus, the photo-etching technique allows both an economical process for producing springs 10 but also allows better control over the manufacturing of the springs 10 than is present with wire wound coil springs.

An additional feature of spring 10 of the present invention applied to the pressure regulating spring of the '083 patent is that the ruby ball of the check valve described in the '083 patent rests on the flat central area 26 at the top of the spring 10 as opposed to having the ball rest in an aperture-like opening such as would be the case with a wound wire spring. The fact that contact between the ball and the spring is on flat central area 26 is important because it allows the rotor of the valve described in the '083 patent to move slightly side to side beneath the ball while still allowing the ball to remain centered in the conical seat. This side-to-side clearance for the rotor is important to allow proper clearance for rotation and to accommodate tolerance-stacking issues related to manufacturability. This feature makes the manufacturing process for this valve much more robust.

The spring 10 made according to the present invention offers many advantages over prior art springs. In particular, the spring 10 made by the present method offers the following advantages, alone and in combination, over springs made by conventional wire winding methods: precision, repeatability, space efficiency, performance and economy.

Although this method of making springs 10 and the resulting springs 10 have great applicability in devices such as the device of the '083 patent, the method and resulting spring 10 have applicability in springs for any purpose.

The description contained herein is intended to be illustrative of the invention and not an exhaustive description. Many variations and alternatives to the disclosed embodiments will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method of making a spring comprising the steps of:
   providing a substrate having a central point for each spring and a peripheral area for each spring spaced away from the central point;
   forming at least one spiral leg in the substrate, the spiral leg having a proximal and a distal end, the spiral leg leaving a central area in the substrate around the central point and a residual area near the peripheral area; and,
   moving the central area away from the residual area until a desired free height is reached between the central area and the peripheral area.

2. A method of making a spring comprising the steps of:
   providing a substrate having a central point for each spring and a peripheral area for each spring spaced away from the central point;

forming an interleaved spiral having at least a first leg and a second leg in the substrate, the first and second leg each having a proximal and a distal end, the interleaved spiral leaving a central area in the substrate around the central point and a residual area near the peripheral area; and, moving the central area away from the residual area until a desired free height is reached between the central area and the peripheral area.

3. The method of claim 2 wherein the step of forming an interleaved spring comprises the step of photo-etching the first and second legs in the material of the substrate.

4. The method of claim 2 wherein the step of forming an interleaved spring comprises the step of punching the first and second legs in the material of the substrate.

5. The method of claim 2 wherein the step of forming an interleaved spring comprises the step of cutting the first and second legs in the material of the substrate.

6. The method of claim 5 wherein the step of cutting the first and second legs includes the step of cutting the first and second legs by means chosen from the group consisting of EDM, laser cutting and water jet cutting.

7. The method of claim 2 wherein the first and second legs are evenly spaced from one another.

8. The method of claim 2 wherein the proximal end and distal end of the first and second leg begin and end on opposite sides of the central point but do not touch.

9. The method of claim 2 wherein the substrate is a metal substrate.

10. The method of claim 9 wherein the metal substrate is chose from a group consisting of stainless steel, nickel chrome alloys, MP35N alloy, nickel-titanium alloys and titanium.

11. The method of claim 2 wherein the substrate has a thickness of between about 0.0005" and 0.005".

12. The method of claim 11 wherein the substrate has a thickness of about 0.001".

13. The method of claim 2 wherein the step of moving the central area away from the residual area until a desired free height is reached between the central area and the peripheral area includes the step of moving a plunger against the central area while capturing or restraining the residual area at or near the peripheral area.

14. The method of claim 2 wherein the step of moving the central area away from the residual area until a desired free height is reached between the central area and the peripheral area includes the step of moving a plunger against the central area while capturing or restraining the residual area at or near the peripheral area.

15. The method of claim 2 wherein the step of moving the central area away from the residual area until a desired free height is reached between the central area and the peripheral area includes the steps of capturing the central area and then moving the central area away from the residual area.

16. The method of claim 2 further comprising the step of forming a hole in the central area.

17. The method of claim 2 wherein the step of forming an interleaved spiral having at least a first leg and a second leg in the substrate includes the step of forming an interleaved spiral having at least a first leg, a second leg and a third leg in the substrate, the first, second and third leg each having a proximal and a distal end, the interleaved spiral leaving a central area in the substrate around the central point and a residual area near the peripheral area.

18. The method of claim 17 wherein the step of step of forming an interleaved spiral having at least a first leg, a second leg and a third leg in the substrate includes the step of forming an interleaved spiral having at least a first leg, a second leg, a third leg and a fourth leg in the substrate, the first, second, third and fourth leg each having a proximal and a distal end, the interleaved spiral leaving a central area in the substrate around the central point and a residual area near the peripheral area.

19. A spring comprising:
a substrate having a central point, a central area in the substrate around the central point, a peripheral area spaced away from the central point and a residual area near the peripheral area;
a spiral leg formed in the substrate, the spiral leg having a proximal and a distal end, the spiral leg leaving the central area and extending to the residual area
whereby the distal end of the spiral leg is connected to the central area and the proximal end of the spiral leg is connected to the residual area,
whereby the spring has a frustro-conical shape and
whereby no two portions of the spiral leg overlap each other.

20. A spring comprising:
a substrate having a central point, a central area in the substrate around the central point, a peripheral area spaced away from the central point and a residual area near the peripheral area;
an interleaved spiral formed in the substrate, the interleaved spiral having at least a first leg and a second leg, the first and second leg each having a proximal and a distal end, the interleaved spiral leaving the central area and extending to the residual area
whereby the distal ends of the first and second leg area are connected to the central area and proximal ends of the first and second leg are connected to the residual area and
whereby the spring has a frustro-conical shape.

21. The spring of claim 20 wherein the interleaved spring is formed by photo-etching the first and second legs in the material of the substrate.

22. The spring of claim 20 wherein the interleaved spring is formed by punching the first and second legs in the material of the substrate.

23. The spring of claim 20 wherein the interleaved spring is formed by cutting the first and second legs in the material of the substrate.

24. The spring of claim 23 wherein the first and second legs are cut by means chosen from the group consisting of EDM, laser cutting and water jet cutting.

25. The spring of claim 20 wherein the first and second legs are evenly spaced from one another.

26. The spring of claim 20 wherein the proximal end and distal end of the first and second leg begin and end on opposite sides of the central point but do not touch.

27. The spring of claim 20 wherein the substrate is a metal substrate.

28. The spring of claim 27 wherein the metal substrate is chose from a group consisting of stainless steel, nickel chrome alloys, MP35N alloy, nickel-titanium alloys and titanium.

29. The spring of claim 20 wherein the substrate has a thickness of between about 0.0005" and 0.005".

30. The spring of claim 29 wherein the substrate has a thickness of about 0.001".

31. The spring of claim 20 wherein the central area has a hole in it.

32. The spring of claim 20 wherein the interleaved spiral further includes a third leg formed in the substrate, the third leg having a proximal and a distal end.

33. The spring of claim 32 wherein the interleaved spiral further includes a fourth leg formed in the substrate, the fourth leg having a proximal and a distal end.

34. A spring made according to the steps of:
providing a substrate having a central point for each spring and a peripheral area for each spring spaced away from the central point;
forming an interleaved spiral having at least a first leg and a second leg in the substrate, the first and second leg each having a proximal and a distal end, the interleaved spiral leaving a central area in the substrate around the central point and a residual area near the peripheral area; and,
moving the central area away from the residual area until a desired free height is reached between the central area and the peripheral area.

35. The spring of claim 34 wherein the step of forming an interleaved spring comprises the step of photo-etching the first and second legs in the material of the substrate.

36. The spring of claim 34 wherein the step of forming an interleaved spring comprises the step of punching the first and second legs in the material of the substrate.

37. The spring of claim 34 wherein the step of forming an interleaved spring comprises the step of cutting the first and second legs in the material of the substrate.

38. The spring of claim 37 wherein the step of cutting the first and second legs includes the step of cutting the first and second legs by means chosen from the group consisting of EDM, laser cutting and water jet cutting.

39. The spring of claim 34 wherein the first and second legs are evenly spaced from one another.

40. The spring of claim 34 wherein the proximal end and distal end of the first and second leg begin and end on opposite sides of the central point but do not touch.

41. The spring of claim 34 wherein the substrate is a metal substrate.

42. The spring of claim 41 wherein the metal substrate is chose from a group consisting of stainless steel, nickel chrome alloys, MP35N alloy, nickel-titanium alloys and titanium.

43. The spring of claim 34 wherein the substrate has a thickness of between about 0.0005" and 0.005".

44. The spring of claim 43 wherein the substrate has a thickness of about 0.001".

45. The spring of claim 34 wherein the step of moving the central area away from the residual area until a desired free height is reached between the central area and the peripheral area includes the step of moving a plunger against the central area while capturing or restraining the residual area at or near the peripheral area.

46. The spring of claim 34 wherein the step of moving the central area away from the residual area until a desired free height is reached between the central area and the peripheral area includes the step of moving a plunger against the central area while capturing or restraining the residual area at or near the peripheral area.

47. The spring of claim 34 wherein the step of moving the central area away from the residual area until a desired free height is reached between the central area and the peripheral area includes the steps of capturing the central area and then moving the central area away from the residual area.

48. The spring of claim 34 further comprising the step of forming a hole in the central area.

49. The spring of claim 34 wherein the step of forming an interleaved spiral having at least a first leg and a second leg in the substrate includes the step of forming an interleaved spiral having at least a first leg, a second leg and a third leg in the substrate, the first, second and third leg each having a proximal and a distal end, the interleaved spiral leaving a central area in the substrate around the central point and a residual area near the peripheral area.

50. The spring of claim 49 wherein the step of step of forming an interleaved spiral having at least a first leg, a second leg and a third leg in the substrate includes the step of forming an interleaved spiral having at least a first leg, a second leg, a third leg and a fourth leg in the substrate, the first, second, third and fourth leg each having a proximal and a distal end, the interleaved spiral leaving a central area in the substrate around the central point and a residual area near the peripheral area.

* * * * *